(12) United States Patent
Chatburn et al.

(10) Patent No.: US 8,550,077 B2
(45) Date of Patent: Oct. 8, 2013

(54) VENTILATOR CONTROL SYSTEM UTILIZING A MID-FREQUENCY VENTILATION PATTERN

(75) Inventors: Robert L. Chatburn, Cleveland Heights, OH (US); Eduardo Mireles-Cabodevila, Little Rock, AR (US)

(73) Assignee: The Cleveland Clinic Foundation, Cleveland, OH (US)

( * ) Notice: Subject to any disclaimer, the term of this patent is extended or adjusted under 35 U.S.C. 154(b) by 418 days.

(21) Appl. No.: 12/783,179

(22) Filed: May 19, 2010

(65) Prior Publication Data
US 2010/0300445 A1 Dec. 2, 2010

Related U.S. Application Data (60) Provisional application No. 61/179,550, filed on May 19, 2009.

(51) Int. Cl.
*A61M 16/00* (2006.01)
*A62B 7/00* (2006.01)
*F16K 31/02* (2006.01)

(52) U.S. Cl.
USPC ............ 128/204.23; 128/204.18; 128/204.21; 137/908

(58) Field of Classification Search
USPC ................. 128/202.22, 204.18, 204.21–23, 128/205.23, 203.12–203.14, 205.13–205.18, 128/205.24, 206.28–206.29, 207.12, 128/207.14–207.16, 898; 137/908
See application file for complete search history.

(56) References Cited

U.S. PATENT DOCUMENTS

| | | | |
|---|---|---|---|
| 5,429,123 A * | 7/1995 | Shaffer et al. ............ | 128/204.23 |
| 7,222,623 B2 * | 5/2007 | DeVries et al. .......... | 128/204.18 |
| 2005/0109340 A1 * | 5/2005 | Tehrani ..................... | 128/204.21 |
| 2008/0202520 A1 * | 8/2008 | Mitton et al. ............. | 128/204.21 |

OTHER PUBLICATIONS

Hardin et al., "Mid-Frequency Ventilation in Acute Respiratory Distress Syndrome: The New Wave . . . length?", Respiratory Care, 2008; 53 (12): 1655-56.*

Mireles-Cabodevila et al., "Mid-Frequency Ventilation: Unconventional Use of Conventional Mechanical Ventilation as a Lung-Protection Strategy", *Respiratory Care*, 2008;53(12):1669-1677.

* cited by examiner

*Primary Examiner* — Jackie Ho
*Assistant Examiner* — Mark K Han
(74) *Attorney, Agent, or Firm* — Tarolli, Sundheim, Covell & Tummino LLP (57) ABSTRACT

Systems and methods are provided for providing ventilation to a patient. An air source is configured to provide pressurized air to a patient through a patient circuit according to a ventilation pattern. At least one sensor is configured to monitor a corresponding physiologic property of the patient. A ventilator control system is configured to calculate an alveolar ventilation value from the monitored physiologic property of the patient, determine at least an optimal frequency for the ventilation pattern from the calculated alveolar ventilation value, and update the ventilation pattern according to the determined optimal frequency.

14 Claims, 5 Drawing Sheets

VENTILATOR CONTROL SYSTEM UTILIZING A MID-FREQUENCY VENTILATION PATTERN

RELATED APPLICATION

This application claims priority from U.S. Provisional Application No. 61/179,550, filed May 19, 2009, the subject matter which is incorporated herein by reference in its entirety.

FIELD OF THE INVENTION

The present invention relates to systems and methodologies for providing medical treatment, and, in particular, is directed to systems and methods for controlling a mechanical ventilator to provide mid-frequency operation.

BACKGROUND OF THE INVENTION

Broadly speaking, a medical mechanical ventilator is an automatic machine designed to provide all or part of the work the body must produce to move gas into and out of the lungs. Standard air, oxygen, or a mixture of standard air and oxygen can be provided to the patient at a desired pressure or volume to ensure proper hemodynamic function of the patient. For example, mechanical ventilators can be used in instances of acute lung injury, such as acute respiratory distress syndrome or trauma, apnea with respiratory arrest, chronic obstructive pulmonary disease, acute respiratory acidosis due to paralysis of the diaphragm (e.g., due to Guillain-Barré syndrome, Myasthenia Gravis, spinal cord injury, or the effect of anesthetic and muscle relaxant drugs), neurological disorders, hypoxemia, and hypotension, for example, from sepsis, shock, or congestive heart failure. Given the variety of conditions that can provoke the need for mechanical ventilation, it will be appreciated that the breathing pattern governing the provision of air to the patient will vary significantly with the patient's condition.

SUMMARY OF THE INVENTION

In accordance with an aspect of the present invention, a method is provided for controlling a mechanical ventilator to provide mid-frequency mandatory ventilation to a patient. Mandatory ventilation is provided to a patient according to a ventilation pattern. An alveolar ventilation of the patient is monitored. One of an optimal frequency, an optimal duty cycle, and an optimal positive end expiratory pressure is determined for the mechanical ventilator according to the alveolar ventilation of the patient. The ventilation pattern of the mechanical ventilator is updated to include the determined one of the optimal frequency, the optimal duty cycle, and the optimal positive end expiratory pressure.

In accordance with another aspect of the present invention, a mechanical ventilator system is provided. An air source is configured to provide pressurized air to a patient through a patient circuit according to a ventilation pattern. Sensors are provided to monitor pressure, volume, flow, and exhaled carbon dioxide. A ventilator control system is configured to calculate an alveolar ventilation value from the monitored variables, determine at least an optimal frequency for the ventilation pattern from the calculated alveolar ventilation value, and update the ventilation pattern according to the determined optimal frequency.

In accordance with yet another aspect of the present invention, a computer readable medium is provided. The computer readable medium stores computer executable instructions for controlling a mechanical ventilator to provide mid-frequency mandatory ventilation to a patient, such that, upon execution in a computer processor, the executable instructions are configured to perform an iterative method. In the iterative method, the mechanical ventilator is instructed to provide mandatory ventilation to a patient according to a ventilation pattern, a feedback value representing an alveolar ventilation of the patient is monitored, and a duty cycle of the ventilation pattern is adjusted according to the feedback value. The iterative method is continued until a termination event is detected, such that a plurality of adjusted duty cycles and associated feedback values are collected.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
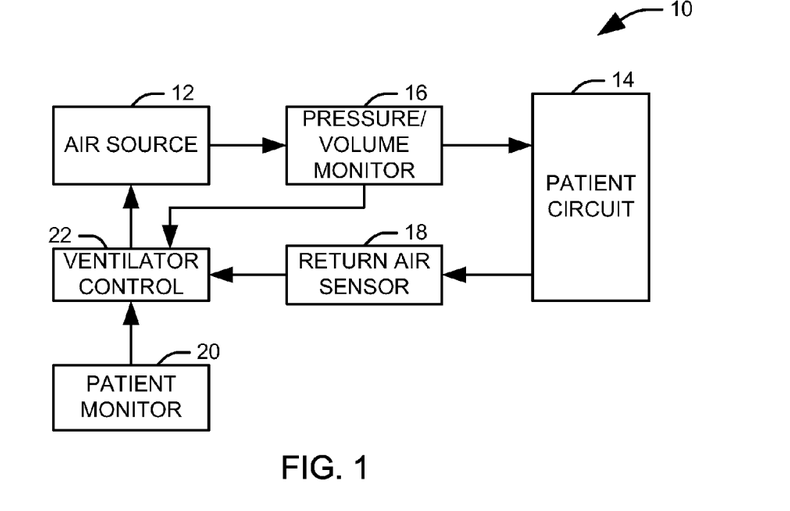
FIG. 1 illustrates a ventilator system utilizing mid-frequency ventilation in accordance with an aspect of the present invention.

FIG. 1 illustrates a ventilator system 10 utilizing a mid-frequency ventilation pattern in accordance with an aspect of the present invention. The ventilator system 10 comprises an air source 12 that is configured to provide pressurized air to a patient's lungs through a patient circuit 14. For example, the air source 12 can include one or more of a pneumatic pump, a turbine, or a pressurized tank of gas controlled by an electrically actuatable flow value such that a desired pressure and volume of air can be provided to the patient. It will be appreciated that the air source 12 can provide room quality air at the desired pressure and volume, but can also, for example, provide an enhanced oxygen mixture or even pure oxygen. The operation of the ventilator 10 can be monitored at a diagnostic pressure and volume monitor 16 to ensure that a desired pressure and volume of air are provided to the patient.

The patient circuit 14 provides a pathway for the pressurized air to the patient's airway (e.g., through the mouth or nose or directly to the patient's lungs). In one implementation, the patient circuit 14 can include a plurality of plastic tubes, comprising a set of one or more tubes for each of a plurality of ventilator functions (e.g., carrying inhaled air, patient pressure, exhaled air, etc.). In general, the natural relaxation of the patient's lungs expels the provided air and returns it to the ventilator for analysis at a return air sensor 18.

In the illustrated implementation, the return air sensor 18 can evaluate the content and pressure of the patient's exhalation to evaluate the gas exchange in the patient's lungs. For example, the return air sensor 18 can include at least one transducer to determine a returned pressure and an infrared sensor that determines the concentration of carbon dioxide in the patient's exhalation by irradiating a sample of the returned air with infrared light of a given frequency and measuring the absorption of the light by the sample.

A patient monitor 20 comprises a plurality of sensors for monitoring hemodynamic properties of the patient. For example, the patient monitor 20 can include a pulse oximeter that estimates a fraction of oxygenated hemoglobin in a patient's arterial blood, a transcutaneous CO2 sensor that estimates the concentration of carbon dioxide in the arterial blood, and an oscillometric blood pressure monitor. Data from each of the patient monitor 20, the returned air sensor 18, and the pressure and volume monitor 16 are provided to a ventilator control 22 in accordance with an aspect of the present invention.

In accordance with an aspect of the present invention, the ventilation control 22 is configured to regulate an operation of the air source 12 as to allow for mid-frequency operation of the ventilator system 10. Specifically, conventional respiratory therapies generally operate at frequencies, that is, numbers of respiratory cycles provided per minute, ranging from around ten to fifteen cycles per minute for a healthy lung to around 35 per minute (for adults) or 60 per minute (for infants) for diseased lungs, for example, respiratory distress syndrome, to deliver conventional tidal volumes (e.g., six to eight milliliters per kilogram for any of the above categories). High frequency ventilation, as understood by one of skill in the art, involves operating a ventilator at very high frequencies (e.g., above 150 per minute), and is generally used for specific therapeutic interventions and for infants. Accordingly, the term mid-frequency operation, as used herein, is meant to encompass the use of ventilator frequencies above those that would be used with conventional tidal volumes, but below the frequencies associated with high frequency interventions (i.e., above 150 per minute). In accordance with an aspect of the present invention, the ventilator control system 22 can provide a mid-frequency ventilation pattern to provide standard respiratory therapy to a patient while maintaining an acceptable positive end expiratory pressure, allowing for a reduced risk of hemodynamic compromise for the patient.

To this end, the ventilator control system 22 can include an optimization system that determines at least an optimal frequency for the ventilator system to reach and maintain a target alveolar ventilation while minimizing the overall tidal volume. For example, the ventilator control system 22 can include one or more expert systems that evaluate the data from each of the patient monitor 20, the returned air sensor 18, and the pressure and volume monitor 16 to dynamically maintain the ventilator pattern at the optimal frequency. The expert systems can further provide for automatic settings for optimum positive end expiratory pressure (PEEP), optimum inspired oxygen concentration, weaning procedures, and patient-ventilator synchrony from parameters provided by the various sensors and monitors 16, 18, and 20. In one implementation, the determined mid-frequency ventilator pattern is designed to maintain a "square wave" pressure waveform, such that a minimum pressure rise time and an appropriate duty cycle for the inspiration is utilized. Once an appropriate ventilator pattern has been determined, the ventilator control system 22 can instruct the air supply 12 to provide air to the patient according to the specified pattern.

Figure 2:
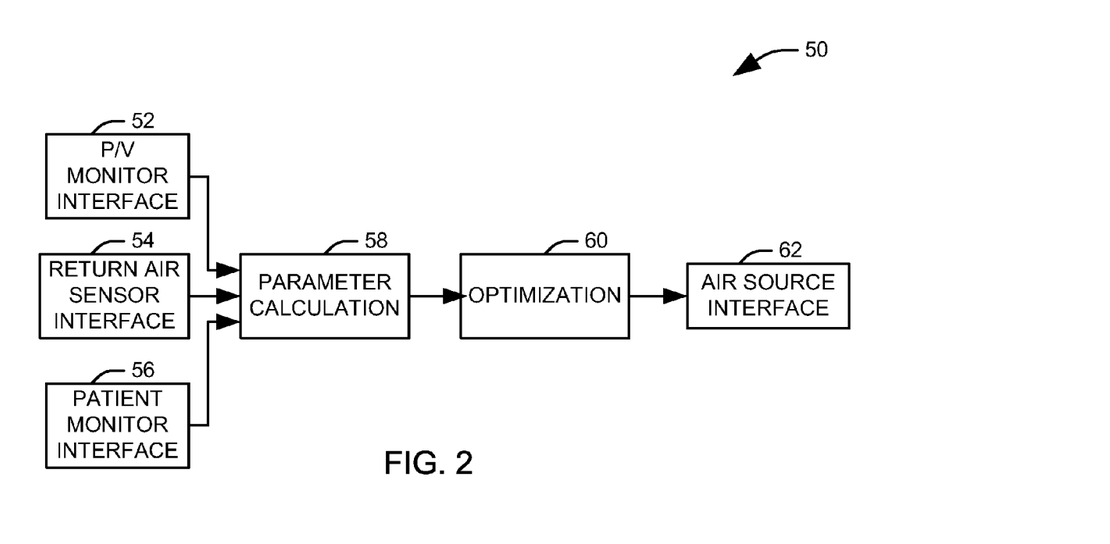
FIG. 2 illustrates an exemplary control system for a ventilator system in accordance with an aspect of the present invention.

FIG. 2 illustrates a control system 50 for a ventilator system in accordance with an aspect of the present invention. The illustrated system 50 receives data representing the function of the ventilator and the hemodynamics of the patient from one or more sensors and determines optimal settings for the ventilator system as to maintain a desired alveolar ventilation while minimizing the overall tidal volume, and the accompanying risk of ventilation induced damage to the lung tissue. To this end, the control system 50 includes a pressure and volume (P/V) monitor interface 52 that receives an input from one or more monitors within the ventilator system. The received data can include the frequency, inspiratory pressure, duty cycle, and tidal volume currently provided by the respirator, essentially characterizing the respiratory input to the patient.

A return air sensor interface 54 receives input from one or more sensors that evaluate the air returned by the patient. For example, the received data can include at least the concentration of carbon dioxide ($CO_2$) in the air exhaled by the patient and an expiratory pressure of the patient. A patient monitor interface 56 can receive data from one or more monitoring devices that evaluate the clinical status of the patient. For example, the patient monitor interface 56 can receive one or more of the current concentrations of carbon dioxide and oxygen in the arterial blood of the patient, a blood pressure of the patient, and a heart rate of the patient.

The data received at each of the pressure and volume monitor interface 52, the return air sensor interface 54, and the patient monitor interface 56 can be provided to a parameter calculation component 58. The parameter calculation component 58 can utilize the received data to calculate at least a minute alveolar ventilation of the patient, for example, as a function of a tidal volume and a ventilator frequency from the pressure and volume monitor interface 52, an end tidal $CO_2$ concentration from the return air sensor interface 54, and an estimated arterial $CO_2$ concentration from the patient monitor interface 56. The calculated minute alveolar ventilation, along with additional parameters calculated at or provided to the parameter calculation component 58, such as the ventilator frequency, the tidal volume, a positive end expiratory pressure (PEEP), a peak inspiratory pressure, an estimated oxygen saturation of the arterial blood, and a duty cycle of the respirator can be provided to an optimization system 60 for analysis.

The optimization system 60 determines one or more optimal parameters for a ventilator system from the parameters provided from the parameter calculation component 58. The optimization system 60 can comprise any appropriate optimization routine, including an artificial neural network or statistical classifier trained on previous patient data, a rule based optimization procedure, or a gradient search of a mathematic model. In one implementation, an adaptive rule based optimization approach is utilized, in which one or more parameters of interest are altered according to the rule based approach and feedback from the ventilator is utilized to navigate the rule based system until a termination condition is achieved. In accordance with an aspect of the present invention, the parameters of interest can include the frequency, tidal volume, and duty cycle of the ventilator as well as a positive end expiratory pressure and peak inspiratory pressure of the patient, with the changes to the parameters of interest designed to maintain a minute alveolar ventilation within a desired range. Once the optimal parameters have been determined, a ventilation pattern for the ventilator system can be determined and provided to the air source at an air source interface.

Figure 3:
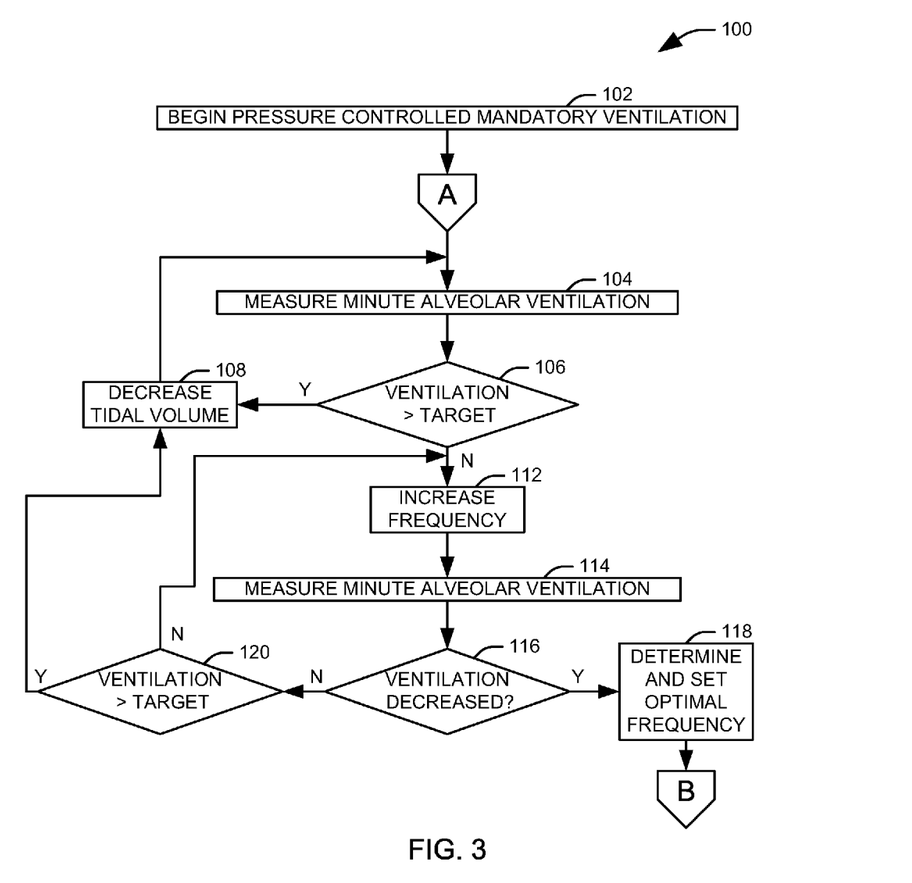
FIG. 3 illustrates an exemplary methodology for optimizing a frequency and tidal volume of a mechanical ventilator in accordance with an aspect of the present invention.
Figure 4:
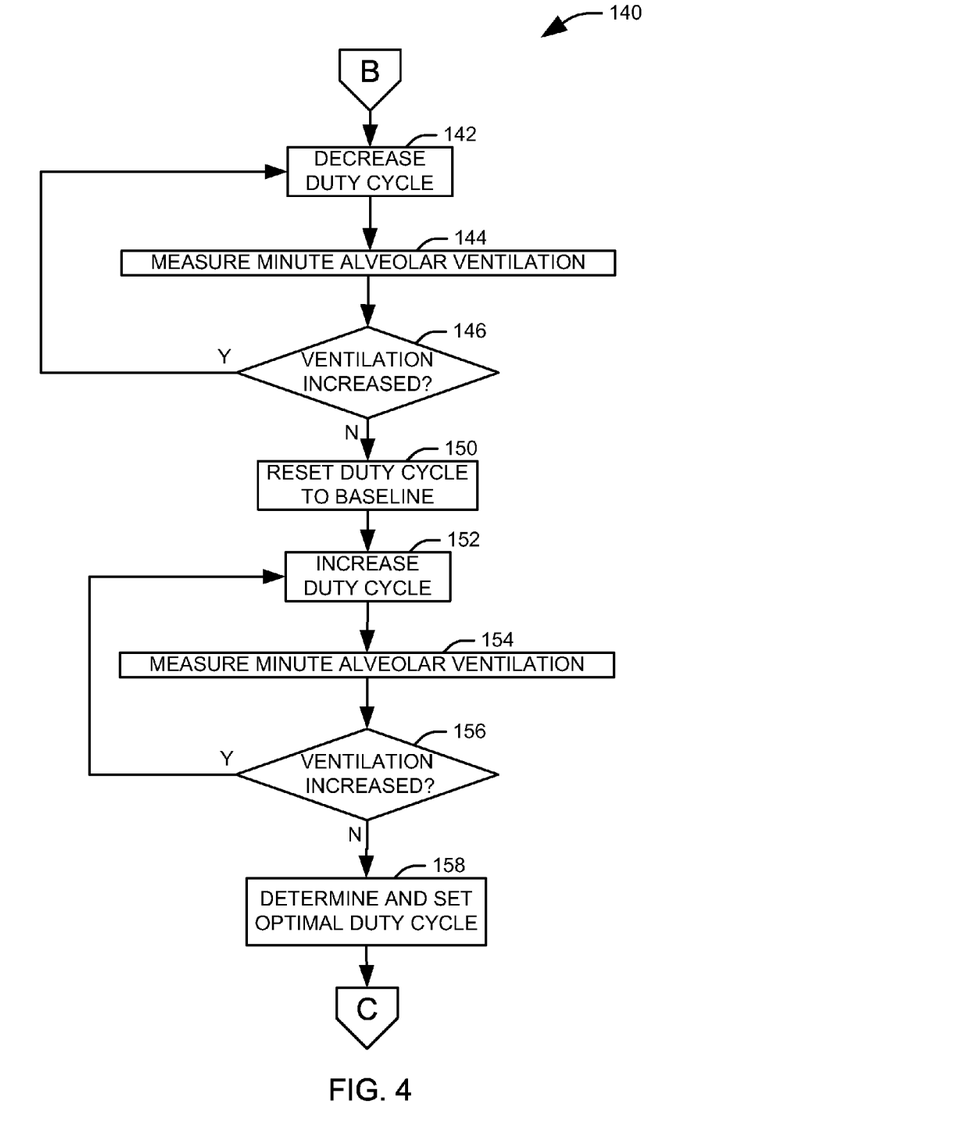
FIG. 4 illustrates an exemplary methodology for optimizing a duty cycle of a mechanical ventilator in accordance with an aspect of the present invention.
Figure 5:
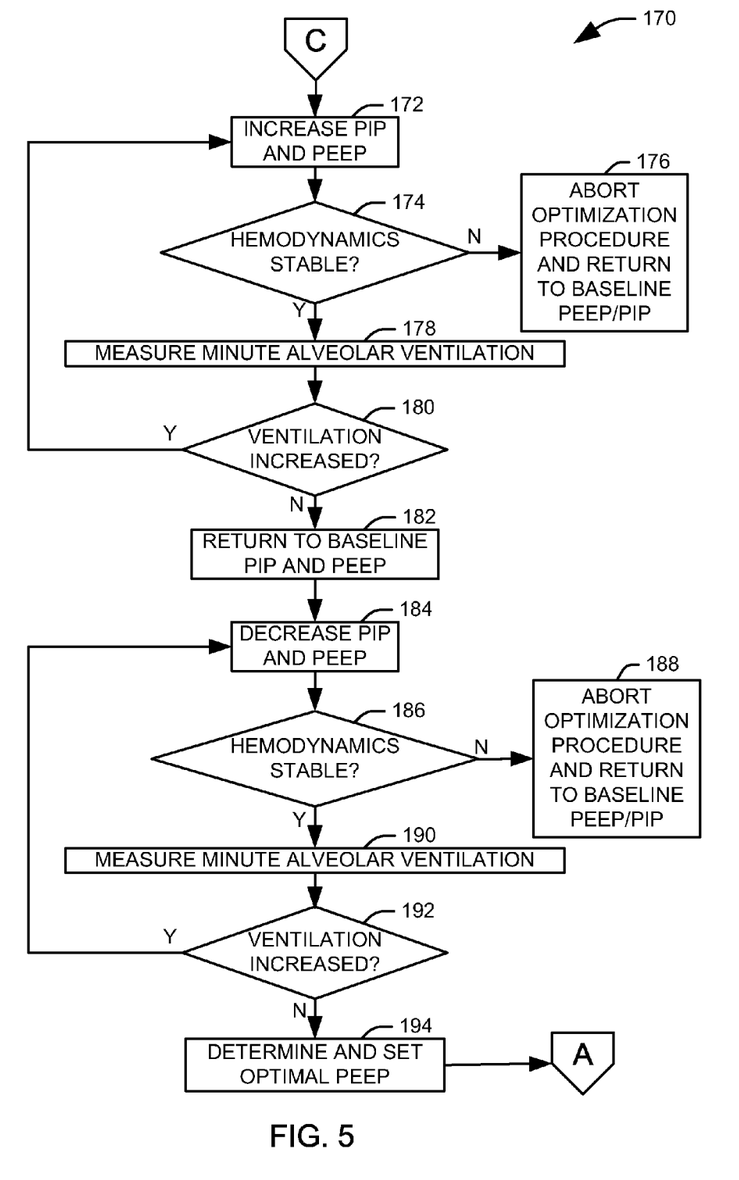
FIG. 5 illustrates an exemplary methodology for optimizing a positive end expiratory pressure and peak inspiratory pressure of a mechanical ventilator in accordance with an aspect of the present invention.

In view of the foregoing structural and functional features described above, a methodology in accordance with various aspects of the present invention will be better appreciated with reference to FIGS. 3-5. While, for purposes of simplicity of explanation, the methodologies of FIG. 3-5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 3 illustrates an exemplary methodology 100 for controlling a ventilator system in accordance with an aspect of the present invention. In accordance with an aspect of the present invention, the methodology 100, along with the methodologies of FIGS. 4 and 5, provide an adaptive optimization scheme for determining an optimal tidal frequency, tidal volume, duty cycle, peak inspiratory pressure, and positive end expiratory pressure as to provide a target alveolar ventilation. At step 102, pressure controlled ventilation is initiated. It will be appreciated that the illustrated methodology is merely exemplary, and that a methodology in accordance with an aspect of the present invention can include any pressure controlled ventilation control scheme that seeks to maximize alveolar ventilation via a mid-frequency approach. Initial parameters for the respiratory cycle can depend on the condition of the patient, but exemplary parameters can include a frequency of fifteen cycles per minute, a duty cycle of fifty percent, and a tidal volume of six milliliters per kilogram of the patient's weight.

At step 104, the minute alveolar ventilation for the patient is computed. It will be appreciated that this measurement can be taken by any clinically appropriate method. In the illustrated example, a concentration of carbon dioxide in the exhaled air of the patient at the end of an exhalation can be measured as an end tidal $CO_2$, for example, by passing infrared light of a particular frequency through a sample of known volume and determining a degree of absorption of the light. An arterial $CO_2$ concentration can also be measured or estimated, for example, from a transcutaneous $CO_2$ monitor. From these values, it is possible to calculate (e.g., via Bohr's equation) a portion of the total tidal volume representing physiological dead space, and thus the total physiological dead space and alveolar volume for each respiratory cycle. For a given frequency, the minute alveolar volume is simply the product of the alveolar volume and the frequency, or the number of respiratory cycles per minute.

At step 106, it is determined if the calculated minute alveolar ventilation is greater than a target range. It will be appreciated that the desired range will vary with the clinical situation of the patient. Representative target values for alveolar value can comprise around 4.6 L/min for a healthy lung to 8.9 L/min for a morbidly obese patient. The desired range can be defined around these target values such that each target value has a small range of tolerance. If the calculated minute alveolar ventilation is greater than a target range (Y), the methodology advances to step 108 where the tidal volume is decreased. The methodology then returns to step 104 to reevaluate the minute alveolar ventilation.

If the calculated minute alveolar ventilation is not greater than the target range (N), the methodology 100 advances to step 112, where the frequency of the respiratory cycle is increased. The minute alveolar ventilation is measured again at step 114, and it is determined at step 116 if the minute alveolar ventilation has decreased from the previous measurement at step 104. If the ventilation has decreased (Y), an optimal frequency can be determined at step 118, for example, as the frequency prior to the increase at step 112, and set as the frequency of the ventilator. The frequency and tidal volume settings that provide a highest minute alveolar ventilation throughout the illustrated methodology 100 can be selected as the optimal value. Alternatively, multiple values for each of the frequency and tidal volume can be collected, for example, as the last two or more values determined by the system, and utilized to obtain optimal values for the frequency and tidal volume via interpolation or averaging. The methodology 100 then continues in FIG. 4, in which the duty cycle of the ventilator is optimized.

If the ventilation has not decreased (N), the methodology advances to step 120, where it is determined if the minute alveolar ventilation has risen above the target range. If the ventilation is above the target range (Y), the methodology returns to step 108 where the tidal volume is reduced, and the methodology proceeds to step 104 to reevaluate the minute alveolar ventilation. If the ventilation does not exceed the target range (N), the methodology returns to step 112, where the frequency is increased and the minute alveolar ventilation is reevaluated.

Once the optimal frequency has been achieved, a duty cycle of the ventilator is optimized in the methodology 140 illustrated in FIG. 4. The methodology 140 begins at step 142, where the duty cycle of the ventilator is reduced by a set amount. At step 144, the minute alveolar ventilation is measured, and it is determined at step 146 if the minute alveolar ventilation has increased since a previous measurement. If the ventilation has increased (Y), the methodology returns to step 142, where the duty cycle is decreased, and the minute alveolar ventilation is reevaluated. If the ventilation has not increased (N), the methodology advances to step 150, where the base duty cycle is restored.

At step 152, the duty cycle is increased by a set amount. At step 154, the minute alveolar ventilation is measured, and it is determined at step 156 if the minute alveolar ventilation has increased since a previous measurement. If the ventilation has increased (Y), the methodology returns to step 152, where the duty cycle is increased and the minute alveolar ventilation is reevaluated. If the ventilation has not increased (N), the methodology advances to step 158, where an optimal duty cycle is determined and set at the ventilator. In one implementation, a duty cycle that provides a highest minute alveolar ventilation throughout the illustrated methodology 140 can be selected as the optimal value. Alternatively, multiple values for the duty cycle can be collected, for example, as the last two or more values determined by the system, and utilized to obtain an optimal value for the duty cycle via interpolation or averaging.

Once the optimal duty cycle has been achieved, and set, the positive end expiratory pressure (PEEP) is optimized in a methodology 170 illustrated in FIG. 5. The methodology 170 begins at step 172, where the positive end expiratory pressure (PEEP) and the peak inspiratory pressure (PIP) are increased by a set amount. At step 174, it is determined if the hemodynamics of the patient are stable. For example, one or more of a mean airway pressure, a blood pressure, a blood oxygenation level (e.g., taken via a transcutaneous pulse oximeter), a heart rate, and any other clinically relevant parameter can be monitored, and if any parameter deviates from a prescribed range, the hemodynamics can be determined to be unstable. If the hemodynamics are found to be unstable (N), the methodology advances to step 176, where the optimization is aborted and both the positive end expiratory pressure and the peak inspiratory pressure are returned to their baseline values. In one implementation, a caregiver can be notified by visible or audible alarm to allow the instability to be addressed, and a standard clinical setting for the patient can be assigned to the ventilator.

If the hemodynamics of the patient are determined to be stable (Y), the methodology advances to step 178 where minute alveolar ventilation is measured. It is then determined at step 180 if the minute alveolar ventilation has increased from a previous measurement. If the ventilation has increased (Y), the methodology returns to step 172, where the positive end expiratory pressure and the peak inspiratory pressure are increased, and the hemodynamics of the patient are reevaluated. If the ventilation has not increased (N), the methodology advances to step 182, where the positive end expiratory pressure and the peak inspiratory pressure are returned to baseline values.

At step 184, where the positive end expiratory pressure and the peak inspiratory pressure are decreased by a set amount. At step 186, it is again determined if the hemodynamics of the patient are stable. If the hemodynamics are found to be unstable (N), the methodology advances to step 188, where the optimization is aborted and both the positive end expiratory pressure and the peak inspiratory pressure are returned to their baseline values. If the hemodynamics of the patient are determined to be stable (Y), the methodology advances to step 190 where minute alveolar ventilation is measured. It is then determined at step 192 if the minute alveolar ventilation has increased from a previous measurement. If the ventilation has increased (Y), the methodology returns to step 184, where the positive end expiratory pressure and the peak inspiratory pressure are decreased, and the hemodynamics of the patient are reevaluated.

If the ventilation has not increased (N), the methodology advances to step 194, where an optimal positive end expiratory pressure is determined and the ventilator is set at the appropriate pressure. In one implementation, a positive end expiratory pressure from the illustrated methodology 170 that provides a highest minute alveolar ventilation while maintaining stable hemodynamics can be selected as the optimal value. Alternatively, multiple values for the positive end expiratory pressure can be collected, for example, as the last two or more values determined by the system, and utilized to obtain an optimal value for the positive end expiratory pressure via interpolation or averaging. Once an optimal value for the positive end expiratory process has been established and set, the optimization methodology returns to the methodology of FIG. 3 to reevaluate the optimal frequency and tidal volume of the ventilator in light of the changes to the positive end expiratory pressure, the peak inspiratory pressure, the duty cycle, and any changes in the patient's condition.

Figure 6:
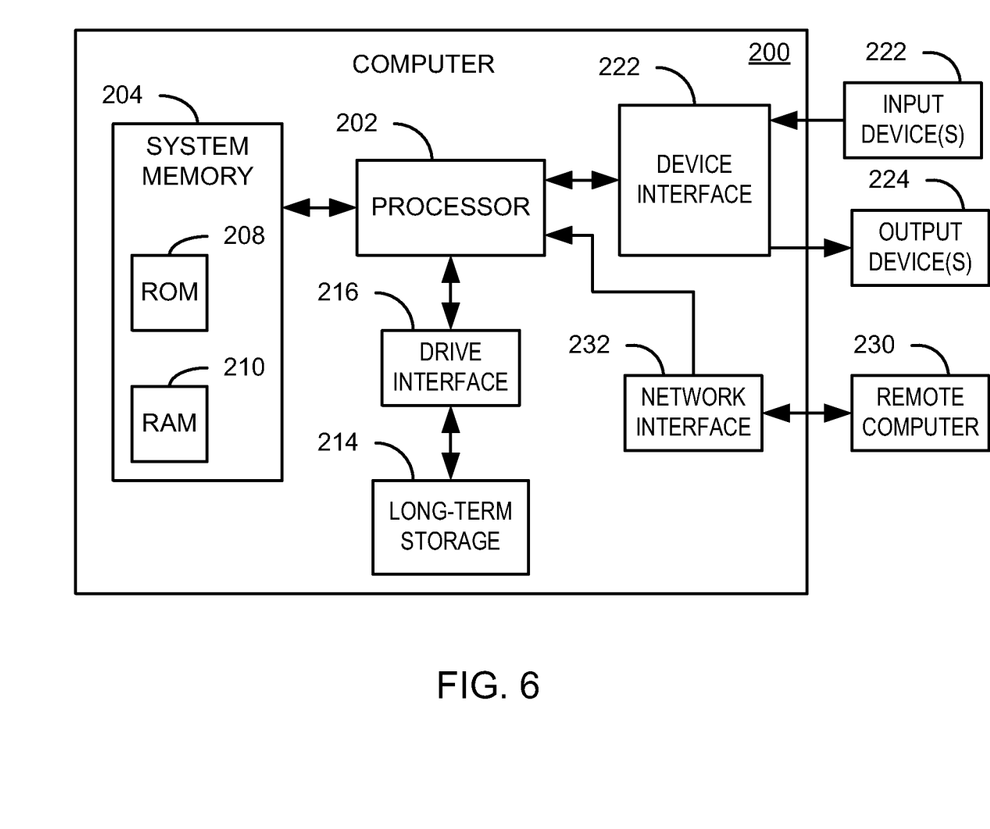
FIG. 6 illustrates a computer system that can be employed to implement systems and methods described herein, such as based on computer executable instructions running on the computer system.

FIG. 6 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) can reside in the ROM 208, generally containing the basic routines that help to transfer information between elements within the computer system 200, such as a reset or power-up.

The computer system 200 can include one or more types of long-term data storage 214, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 202 by a drive interface 216. The long-term storage components 214 provide nonvolatile storage of data, data structures, and computer-executable instructions for the computer system 200. A number of program modules may also be stored in one or more of the drives as well as in the RAM 210, including an operating system, one or more application programs, other program modules, and program data.

A user may enter commands and information into the computer system 200 through one or more input devices 220, such as a keyboard or a pointing device (e.g., a mouse). In accordance with an aspect of the present invention, these input devices can include one or more sensors that monitor the status of a patient and provide physiological data in digital form as feedback to a software control system for a ventilator. It will be appreciated, however, that a ventilator control system in accordance with an aspect of the present invention can, in some implementations, operate as an open loop control system with a standard ventilator system. In such implementations, the physiological feedback provided by the devices is unnecessary. The input devices are often connected to the processor 202 through a device interface 222. For example, the input devices can be connected to the system bus by one or more a parallel port, a serial port or a universal serial bus (USB). One or more output device(s) 224, such as a visual display device or printer, can also be connected to the processor 202 via the device interface 222.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for controlling a mechanical ventilator to provide mid-frequency mandatory ventilation to a patient comprising:

providing ventilation to a patient according to a mid-frequency ventilation pattern;

monitoring an alveolar ventilation of the patient;

iteratively repeating the following steps until a decrease in the alveolar ventilation is recorded after an incremental increase in a respiratory cycle frequency;

(a) incrementally decreasing a tidal volume of the mid-frequency ventilation pattern when the alveolar ventilation is above a target range;

(b) incrementally increasing the respiratory cycle frequency when the alveolar ventilation is not above the target range;

selecting a tidal volume and a respiratory cycle frequency from an iteration immediately prior to the recorded decrease in the alveolar ventilation; and updating the mid-frequency ventilation pattern of the mechanical ventilator to include the selected respiratory cycle frequency and tidal volume.

2. The method of claim 1, further comprising determining the optimal duty cycle, given the selected frequency and tidal volume, for the mechanical ventilator from the monitored alveolar ventilation.

3. The method of claim 2, further comprising determining the optimal positive end expiratory pressure, given the frequency, selected tidal volume, and optimal duty cycle, for the mechanical ventilator from the monitored alveolar ventilation.

4. The method of claim 1, wherein monitoring an alveolar ventilation of the patient comprises:

monitoring an end tidal concentration of carbon dioxide;

monitoring a tidal volume from of air exhaled by the patient;

monitoring a concentration of carbon dioxide in the arterial blood of the patient; and calculating a minute alveolar ventilation from the monitored values of end tidal concentration of carbon dioxide, tidal volume, and the concentration of carbon dioxide in the arterial blood of the patient.

5. A medical ventilator system, comprising:

an air source configured to provide pressurized air to a patient through a patient circuit according to a mid-frequency ventilation pattern;

at least one sensor configured to monitor a corresponding physiologic property of the patient; and a ventilator control system configured to calculate an alveolar ventilation value from the monitored physiologic property of the patient, determine at least an optimal frequency and an optimal duty cycle for the ventilation pattern from the calculated alveolar ventilation value, and update the ventilation pattern according to the determined optimal frequency;

wherein the ventilator control system comprises an adaptive rule based optimization system configured to iteratively alter a frequency associated with the ventilator and adjust the frequency according to feedback from the at least one sensor until a termination condition is achieved.

6. The system of claim 5, the at least one sensor comprising a return air sensor configured to receive air exhaled by the patient and measure a tidal volume and a concentration of carbon dioxide of the returned air.

7. The system of claim 6, the ventilator control system comprising a parameter calculation component configured to calculate a minute alveolar ventilation from the measured tidal volume and concentration of carbon dioxide.

8. The system of claim 5, the ventilator control system being configured to determine an optimal positive end expiratory pressure for the ventilation pattern from the calculated alveolar ventilation value.

9. A non-transitory computer readable medium storing computer executable instructions for controlling a mechanical ventilator to provide mid-frequency ventilation to a patient, such that, upon execution in a computer processor, the executable instructions are configured to perform an iterative method comprising the steps of:

instructing the mechanical ventilator to provide ventilation to a patient according to a mid-frequency ventilation pattern;

monitoring the feedback value representing an alveolar ventilation of the patient; and adjusting a duty cycle of the mid-frequency ventilation pattern according to the feedback value;

wherein the iterative method is continued until a termination event is detected, such that a plurality of adjusted duty cycles and associated feedback values are collected.

10. The non-transitory computer readable medium of claim 9, the executable instructions being configured to, upon the termination event, select an optimal duty cycle from the plurality of adjusted duty cycles according to the associated feedback values and update the ventilation pattern of the mechanical ventilator such that the patient continues to receive ventilation at the selected optimal duty cycle.

11. The non-transitory computer readable medium of claim 9, the iterative method further comprising adjusting a frequency of the ventilation pattern according to the feedback value, such that a plurality of adjusted frequencies and associated feedback values are collected, the executable instructions being configured to, upon the termination event, select an optimal frequency from the plurality of adjusted frequencies according to the associated feedback values and update the ventilation pattern of the mechanical ventilator such that the patient continues to receive ventilation at the selected optimal frequency.

12. The non-transitory computer readable medium of claim 9, the iterative method further comprising adjusting a positive end expiratory pressure of the ventilation pattern according to the feedback value, such that a plurality of adjusted positive end expiratory pressures and associated feedback values are collected, the executable instructions being configured to, upon the termination event, select an optimal positive end expiratory pressure from the plurality of adjusted positive end expiratory pressures according to the associated feedback values and update the ventilation pattern of the mechanical ventilator such that the patient continues to receive ventilation at the selected optimal end expiratory pressure.

13. The non-transitory computer readable medium of claim 9, wherein adjusting a duty cycle of the ventilation pattern according to a feedback value during the iterative method comprises decreasing the duty cycle of the ventilation pattern by a predetermined amount until the feedback value indicates no increase in alveolar ventilation.

14. The non-transitory computer readable medium of claim 13, wherein adjusting a duty cycle of the ventilation pattern according to a feedback value during the iterative method further comprises returning the duty cycle to a baseline value and increasing the duty cycle of the ventilation pattern by a predetermined amount until the feedback value indicates no increase in alveolar ventilation.

* * * * *